(12) United States Patent
Marquez

(10) Patent No.: US 10,117,785 B2
(45) Date of Patent: Nov. 6, 2018

(54) BREASTMILK ABSORBING SYSTEM

(71) Applicant: Nicole Marquez, Fox Lake, IL (US)

(72) Inventor: Nicole Marquez, Fox Lake, IL (US)

( * ) Notice: Subject to any disclaimer, the term of this patent is extended or adjusted under 35 U.S.C. 154(b) by 309 days.

(21) Appl. No.: 15/061,093

(22) Filed: Mar. 4, 2016

(65) Prior Publication Data

US 2017/0252222 A1 Sep. 7, 2017

(51) Int. Cl.
*A61F 13/15* (2006.01)
*A61F 13/14* (2006.01)
*A41D 1/215* (2018.01)
*A61F 13/505* (2006.01)

(52) U.S. Cl.
CPC .......... *A61F 13/141* (2013.01); *A41D 1/215* (2018.01); *A61F 13/14* (2013.01); *A61F 13/145* (2013.01); *A61F 13/505* (2013.01); *A61F 2013/15016* (2013.01)

(58) Field of Classification Search
CPC .......... A61F 2013/15016; A61F 13/14; A61F 13/145; A61F 13/505; A41D 1/215

USPC .................................. 604/385.14, 385.19
See application file for complete search history.

(56) References Cited

U.S. PATENT DOCUMENTS

| | | |
|---|---|---|
| 5,931,717 A | 8/1999 | Lidji |
| 6,015,331 A | 1/2000 | Ioakim |
| D433,786 S | 11/2000 | Gladstone |
| 6,983,489 B2 | 1/2006 | Capiro |
| 7,776,019 B2 | 8/2010 | Kawakami et al. |
| 7,878,880 B2 | 2/2011 | Hendrickson |
| 2012/0046627 A1 | 2/2012 | Agnew |

FOREIGN PATENT DOCUMENTS

WO  WO2009132086  10/2009

*Primary Examiner* — Jacqueline Stephens

(57) ABSTRACT

A breast milk absorbing system includes a nursing garment being that may be worn by a nursing female. The nursing garment has a pouch. An absorbing unit is provided. The absorbing unit is removably positioned within the pouch. The absorbing may absorb breast milk from the nursing female. Thus, the nursing garment is inhibited from becoming wet with the breast milk. The absorbing unit extends across an entire width of the pouch. Thus, the absorbing unit remains aligned with the nursing female's breasts.

4 Claims, 3 Drawing Sheets

BREASTMILK ABSORBING SYSTEM

BACKGROUND OF THE DISCLOSURE

Field of the Disclosure

The disclosure relates to absorbing devices and more particularly pertains to a new absorbing device for absorbing breast milk that leaks from a nursing female.

SUMMARY OF THE DISCLOSURE

An embodiment of the disclosure meets the needs presented above by generally comprising a nursing garment being that may be worn by a nursing female. The nursing garment has a pouch. An absorbing unit is provided. The absorbing unit is removably positioned within the pouch. The absorbing may absorb breast milk from the nursing female. Thus, the nursing garment is inhibited from becoming wet with the breast milk. The absorbing unit extends across an entire width of the pouch. Thus, the absorbing unit remains aligned with the nursing female's breasts.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
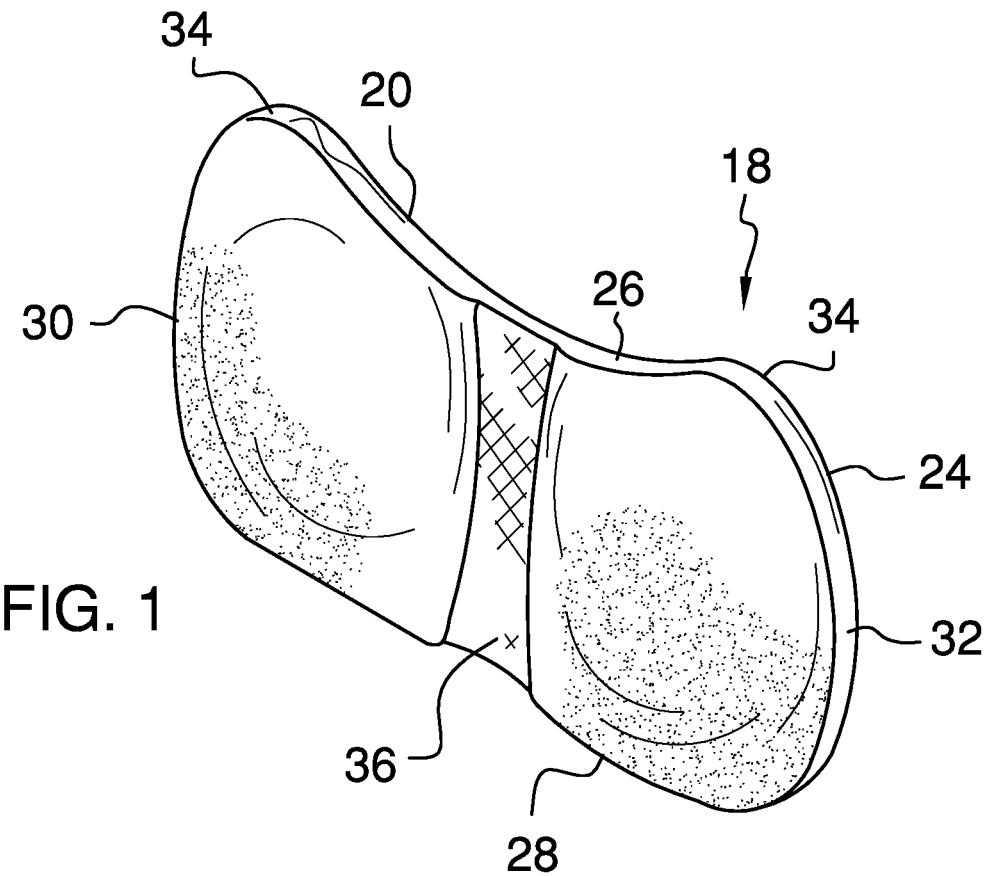
FIG. 1 is a front perspective view of a breast milk absorbing system according to an embodiment of the disclosure.
Figure 2:
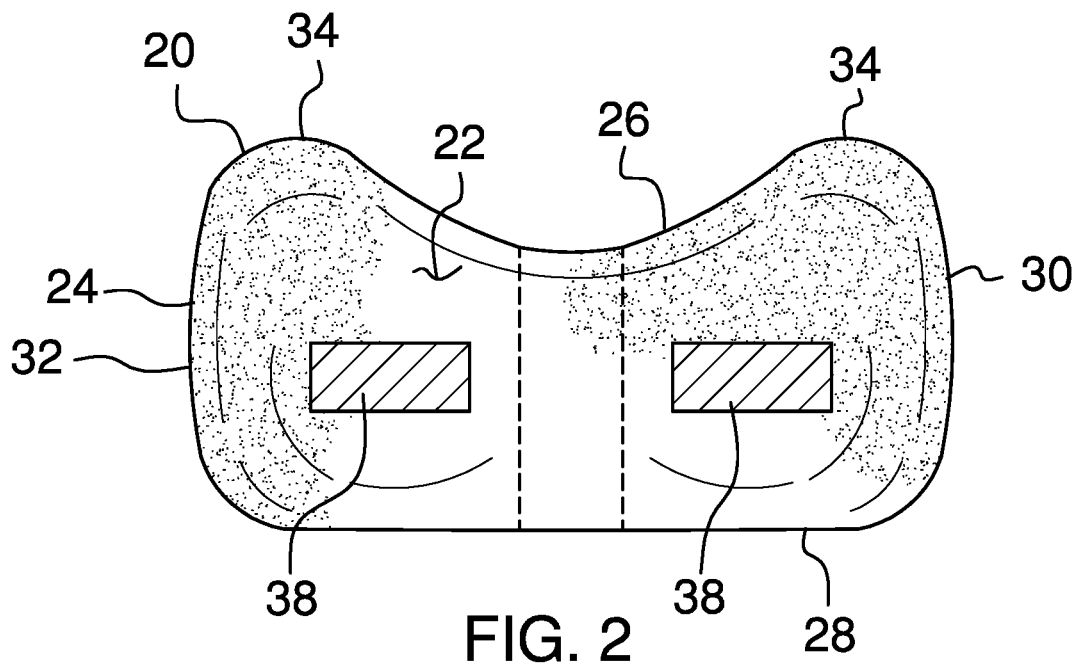
FIG. 2 is a back view of an embodiment of the disclosure.
Figure 3:
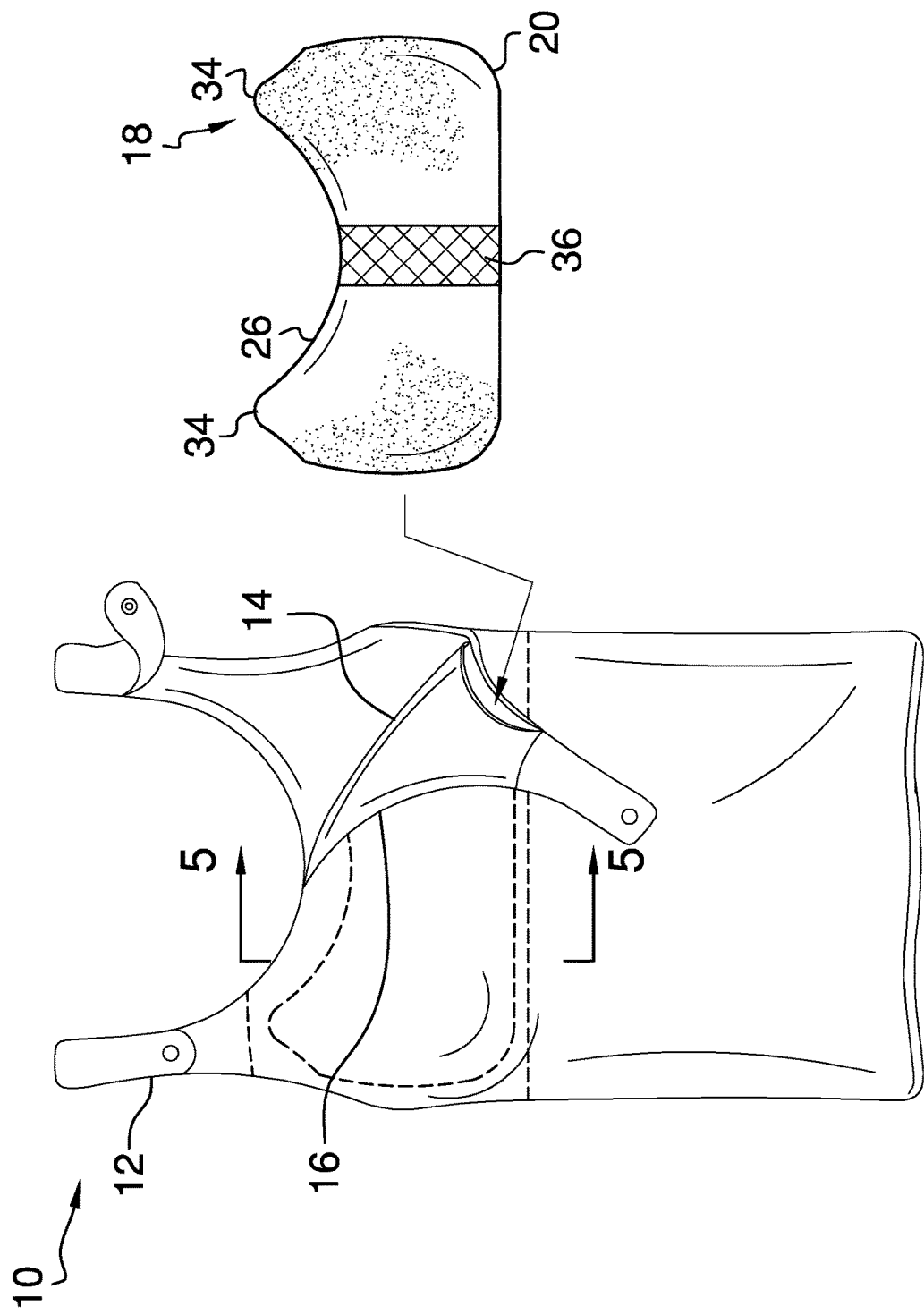
FIG. 3 is a exploded in-use view of an embodiment of the disclosure.
Figure 4:
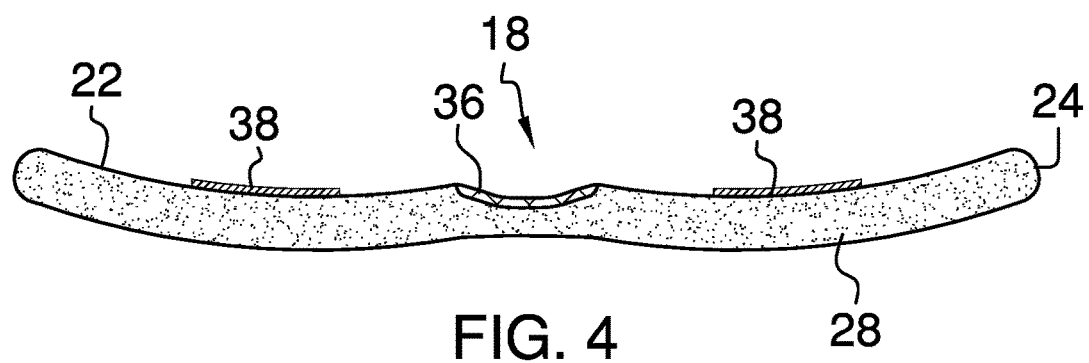
FIG. 4 is a bottom view of an embodiment of the disclosure.
Figure 5:
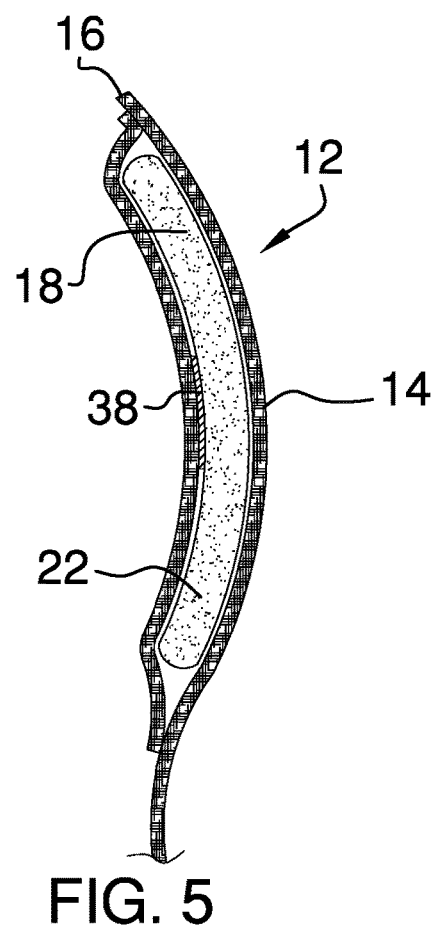
FIG. 5 is a cross sectional taken along line 5-5 of FIG. 3 of an embodiment of the disclosure.

With reference now to the drawings, and in particular to FIGS. 1 through 5 thereof, a new absorbing device embodying the principles and concepts of an embodiment of the disclosure and generally designated by the reference numeral 10 will be described.

As best illustrated in FIGS. 1 through 5, the breast milk absorbing system 10 generally comprises a nursing garment 12 that may be worn by a nursing female. The nursing garment 12 may have a pouch 14 and the pouch 14 may have a top edge 16. The pouch 14 may extend across a chest of the nursing female. The nursing garment 12 may be a nursing shirt or the like.

An absorbing unit 18 is provided and the absorbing unit 18 is removably positionable within the pouch 14. The absorbing unit 18 may absorb breast milk from the nursing female. Thus, the nursing garment 12 is inhibited from becoming wet with the breast milk. The absorbing unit 18 extends across an entire width of the nursing garment 12. Thus, the absorbing unit 18 remains aligned with the nursing female's breasts.

The absorbing unit 18 comprises a pad 20 that has a rear surface 22 and a peripheral edge 24. The peripheral edge 24 has a top side 26, a bottom side 28, a first lateral side 30 and a second lateral side 32. The top side 26 is concavely arcuate between the first lateral side 30 and the second lateral side 32 to define a pair of horns 34 on the pad 20. Each of the horns 34 engages the top edge 16 of the pouch 14 when the pad 20 is positioned in the pouch 14. Thus, the pad 20 is inhibited from sliding laterally in the pouch 14. The pad 20 is comprised of an absorbent material to absorb the breast milk.

A mesh 36 is coupled to the rear surface 22 of the pad 20 and the mesh 36 is centrally positioned on the pad 20. The mesh 36 extends between the top side 26 and the bottom side 28 of the pad 20. The mesh 36 is comprised of a flexible material such that the pad 20 is bendable along the mesh 36. The mesh 36 may be recessed in the rear surface 22 of the pad 20. The rear surface 22 of the pad 20 may be scalloped between the mesh 36 and each of the first lateral side 30 and the second lateral side 32.

A pair of adhesive pads 38 is provided. Each of the adhesive pads 38 is coupled to the rear surface 22 of the pad 20. Each of the adhesive pads 38 adhesively engages the pouch 14 when the pad 20 is positioned within the pouch 14. Thus, the pad 20 is removably coupled to the nursing garment 12.

In use, the nursing garment 12 is worn while the nursing female is nursing. The pad 20 is positioned within the pouch 14 while the nursing female is nursing. Each of the horns 34 on the pad 20 engages the top edge 16 of the pouch 14. Thus, the pad 20 is continuously aligned with the nursing female's breasts. The pad 20 inhibits the nursing garment from becoming soaked with breast milk. The pad 20 is removed from the nursing garment 12 and the pad 20 is discarded when the pad 20 becomes soaked with breast milk.

With respect to the above description then, it is to be realized that the optimum dimensional relationships for the parts of an embodiment enabled by the disclosure, to include variations in size, materials, shape, form, function and manner of operation, system and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A breast milk absorbing system comprising:
a nursing garment being configured to be worn by a nursing female, said nursing garment having a pouch; and
an absorbing unit being removably positioned within said pouch wherein said absorbing unit is configured to absorb breast milk from the nursing female thereby inhibiting the nursing garment from becoming wet with the breast milk, said absorbing unit extending across an entire width of said pouch wherein said absorbing unit is configured to remain aligned with the nursing female's breasts, wherein said absorbing unit comprises a pad having a rear surface and a peripheral edge, said peripheral edge having a top side, a bottom side, a first lateral side and a second lateral side, said top side being concavely arcuate between said first lateral side and said second lateral side to define a pair of horns on said pad, each of said horns engaging a top edge of said pouch such that said pad is inhibited from sliding laterally in said pouch, said pad being comprised of an absorbent material wherein said pad is configured to absorb the breast milk.

2. The system according to claim 1, further comprising:
said absorbing unit includes a pad having a rear surface, a top side and a bottom side; and
a mesh being coupled to said rear surface of said pad, said mesh being centrally positioned on said pad, said mesh extending between said top side of said pad and said bottom side of said pad, said mesh being comprised of a flexible material such that said pad is bendable along said mesh.

3. The system according to claim 2, further comprising a pair of adhesive pads, each of said adhesive pads being coupled to said rear surface of said pad, each of said adhesive pads adhesively engaging said pouch when said pad is positioned within said pouch such that said pad is removably coupled to said nursing garment.

4. A breast milk absorbing system comprising:
a nursing garment being configured to be worn by a nursing female, said nursing garment having a pouch, said pouch having a top edge, said pouch being configured to extend across a chest of the nursing female; and
an absorbing unit being removably positioned within said pouch wherein said absorbing unit is configured to absorb breast milk from the nursing female thereby inhibiting the nursing garment from becoming wet with the breast milk, said absorbing unit extending across an entire width of said pouch wherein said absorbing unit is configured to remain aligned with the nursing female's breasts, said absorbing unit comprising:
a pad having a rear surface and a peripheral edge, said peripheral edge having a top side, a bottom side, a first lateral side and a second lateral side, said top side being concavely arcuate between said first lateral side and said second lateral side to define a pair of horns on said pad, each of said horns engaging said top edge of said pouch such that said pad is inhibited from sliding laterally in said pouch, said pad being comprised of an absorbent material wherein said pad is configured to absorb the breast milk,
a mesh being coupled to said rear surface of said pad, said mesh being centrally positioned on said pad, said mesh extending between said top side and said bottom side of said pad, said mesh being comprised of a flexible material such that said pad is bendable along said mesh, and
a pair of adhesive pads, each of said adhesive pads being coupled to said rear surface of said pad, each of said adhesive pads adhesively engaging said pouch when said pad is positioned within said pouch such that said pad is removably coupled to said nursing garment.

\* \* \* \* \*